US00PP13291P2

(12) United States Plant Patent
Meilland

(10) Patent No.: US PP13,291 P2
(45) Date of Patent: Nov. 26, 2002

(54) MINIATURE ROSE PLANT NAMED 'MEIDARIN'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 15 days.

(21) Appl. No.: 09/709,540

(22) Filed: Nov. 13, 2000

(51) Int. Cl.[7] ..... A01H 5/00
(52) U.S. Cl. ..... Plt./116
(58) Field of Search ..... Plt./116, 118, 119, Plt./120, 123, 125, 126

(56) References Cited

U.S. PATENT DOCUMENTS

PP5,044 P * 5/1983 Saville ..... Plt./116
PP7,424 P * 1/1991 Saville ..... Plt./116

OTHER PUBLICATIONS

Protection Des Obtentions Vegetales, Bulletin Officiel du Comité de la Protection des Obtentions Végétales, No. 4, Cover Page and pp. 124, 131, 136, and 142 (1999).

Protection Des Obtentions Vegetales, Bulletin Officiel du Comité de la Protection des Obtentions Végétales, No. 7, Cover Page and pp. 288 and 293 (1999).

UPOV–ROM, 2001/04, Plant Variety Database, GTI Jouve Retrieval Software, citation for 'MEIdarin'.*

"Plant Patent Director", 1990, American Association of Nurserymen, Washington, D.C., p. 0052.*

Haring, ed., "MODERN ROSES 9", 1986, The American Rose Society, Shreveport, Louisiana, p. 190.*

* cited by examiner

*Primary Examiner*—Howard J. Locker
(74) *Attorney, Agent, or Firm*—Burns, Doane, Swecker & Mathis, LLP

(57) ABSTRACT

A new and distinct variety of rose plant of the dwarf Miniature Class is provided which abundantly forms attractive bicolored double orange suffused with orange-red blossoms. The growth habit is bushy. Very dense medium green glossy foliage is formed that contrasts nicely with the blossom coloration. The new variety is well suited for pot forcing under greenhouse growing conditions to form a distinctive gift plant.

1 Drawing Sheet

BOTANICAL/COMMERCIAL CLASSIFICATION

Miniature Rose Plant Named 'Meidarin'.

SUMMARY OF THE INVENTION

The new variety of *Rosa hybrida* Miniature rose plant was created by artificial pollination wherein two parents were crossed which previously had been studied in the hope that they would contribute the desired characteristics. The female parent (i.e., the seed parent) of the new variety was the product of the cross of the 'Savamark' variety (U.S. Plant Pat. No. , 5,044) and the 'Savabear' variety (U.S. Plant Pat. No. 7,424). The male parent (i.e., the pollen parent) was the 'Meicofum' variety (U.S. Plant Pat. No. 9,997). The parentage of the new variety can be summarized as follows:

('Savamark'×'Savabear')×'Meicofum'.

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) Exhibits a bushy growth habit,
(b) Forms in abundance attractive double orange suffused with orange-red blossoms,
(c) Forms very dense medium green glossy foliage, and
(d) Is well suited for pot forcing.

The new variety well meets the needs of the horticultural industry. It is particularly well suited for pot forcing under greenhouse growing conditions to form a distinctive gift plant.

The new variety can be readily distinguished from its ancestors. More specifically, the 'Savamark' variety forms brilliant orange-red flowers, the 'Savabear' variety forms orange-brown flowers, and the 'Meicofum' variety is a Hybrid Tea with much larger flowers.

The new variety has been found to undergo asexual propagation in France by a number of routes, including budding, grafting, and cuttage. Asexual propagation by the above-mentioned methods as performed in the South of France has shown that the characteristics of the new variety are strictly transmissible from one generation to another.

The new variety has been named the 'Meidarin' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during June while growing on their own roots in greenhouses at LeCannet des Maures, Var, France. Dimensions in centimeters are shown at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower — plan view—obverse;

FIG. 7—illustrates a specimen of an open flower — plan view—reverse;

FIG. 8—illustrates a specimen of a fully open flower — plan view—obverse;

FIG. 9—illustrates a specimen of a fully open flower — plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimen of two leaves with three leaflets — plan view — upper surface (left), and — under surface (right);

FIG. 15—illustrates specimens of two leaves with five leaflets — plan view — upper surface (top), and — under surface (bottom); and FIG. 16—illustrates specimens of two leaves with seven leaflets — plan view — upper surface (top), and — under surface (bottom).

DETAILED DESCRIPTION

The chart used in the identification of the colors is that of The Royal Horticultural Society (R.H.S. Colour Chart). The description is based on the observation of one-year-old specimens of the new variety which were observed during October while growing on their own roots in greenhouses at LeCannet des Maures, Var, France.

Class: Dwarf miniature.

Plant:

*Height.*—Approximately 30 to 40 cm. on average at the end of the growing season.

*Width.*—Approximately 30 cm on average at the end of the growing season.

*Habit.*—Bushy.

Branches:

*Color.*—Young stems: near Yellow-Green Group 146B. Adult wood: near Yellow-Green Group 146A.

*Thorns.*—Size: medium. Quantity: moderately numerous (as illustrated). Color: near Yellow-Green Group 153D with some coloration near Red Group 49B. Configuration: fairly straight on the upper surface and slightly concave on the under surface with an obovate base.

Leaves:

*Petioles.*—Upper surface: non-glandular, and near Yellow-Green Group 146B in coloration. Under surface: near Yellow-Green Group 147B in coloration.

*Stipules.*—Adnate, pectinate, and rather broad.

*Leaflets.*—Number: 3, 5, and 7. Shape: with a narrow symmetrical tip and a wedge-shaped base (as illustrated). Texture: consistent. Serration: regular. General appearance: very dense, medium green and glossy. Color (young foliage): upper surface: near Yellow-Green Group 147A with some reddish anthocyanin coloration of Greyed-Red Group 178A. under surface: near Yellow-Green Group 146B with some reddish anthocyanin coloration of Greyed-Red Group 178A. Color (adult foliage): upper surface: near Yellow-Green Group 147A. under surface: near Yellow-Green Group 146B.

Inflorescence:

*Number of flowers.*—Commonly approximately 1 to 5 per stem.

*Peduncle.*—Near Yellow-Green Group 147B to 147D with some reddish anthocyanin coloration of Greyed-Red Group 178A, and the length commonly is approximately 4.5 to 5 cm on average.

*Sepals.*—Upper surface: tomentose and near Yellow-Green Group 147C and 147D with some reddish anthocyanin coloration of Greyed-Red Group 178A. Under surface: glabrous, and near Yellow-Green Group 146A with some reddish anthocyanin coloration. Shape: with some thin weak extensions (as illustrated).

*Buds.*—Shape: elongated. Size: medium for class, and approximately 2.5 cm in length.

*Flower.*—Form: double and cup-shaped. Diameter: approximately 7 cm on average when fully open. Color (when opening begins): upper surface: near Orange Group 26A and widely suffused with Orange-Red Group 32A. under surface: near Yellow Group 13A and lightly suffused and bordered with Orange-Red Group 30A. Color (when blooming): upper surface: near Orange Group 26A and widely suffused with Orange-Red Group 32A. under surface: near Yellow Group 13A and lightly suffused and bordered with Orange-Red Group 30A. Color (at end of opening): upper surface: near Orange Group 26A and widely suffused with Orange-Red Group 32A. under surface: near Yellow Group 13A and lightly suffused and bordered with Orange-Red Group 30A. Fragrance: none. Anthers: yellow in coloration. Pollen: near Yellow-Orange Group 15A in coloration. Stamen number: approximately 42 on average. Filaments: yellow in coloration. Pistil number: approximately 40 on average. Petal number: approximately 66 on average. Petal configuration: wedge-shaped base and a reflexed tip. Petal drop: very good, the petals detach cleanly. Stigmas: whitish in coloration. Styles: whitish in coloration. Receptacle: medium green, near Yellow-Green Group 146A with some reddish anthocyanin coloration. Lasting quality: approximately 10 days on the plant. The lasting quality has not been evaluated when cut and placed in a vase. Petal drop: good, the petals detach well. Hips: none observed to date.

Development:

*Vegetation.*—Strong and vigorous.

*Blooming.*—Very abundant.

*Resistance to diseases.*—Good with respect to Black Spot.

I claim:

1. A new and distinct variety of Miniature rose plant characterized by the following combination of characteristics:

(a) Exhibits a bushy growth habit,
(b) Forms in abundance attractive bicolored double orange suffused with orange-red blossoms,
(c) Forms very dense medium green glossy foliage, and
(d) Is well suited for pot forcing;

substantially as herein shown and described.

* * * * *

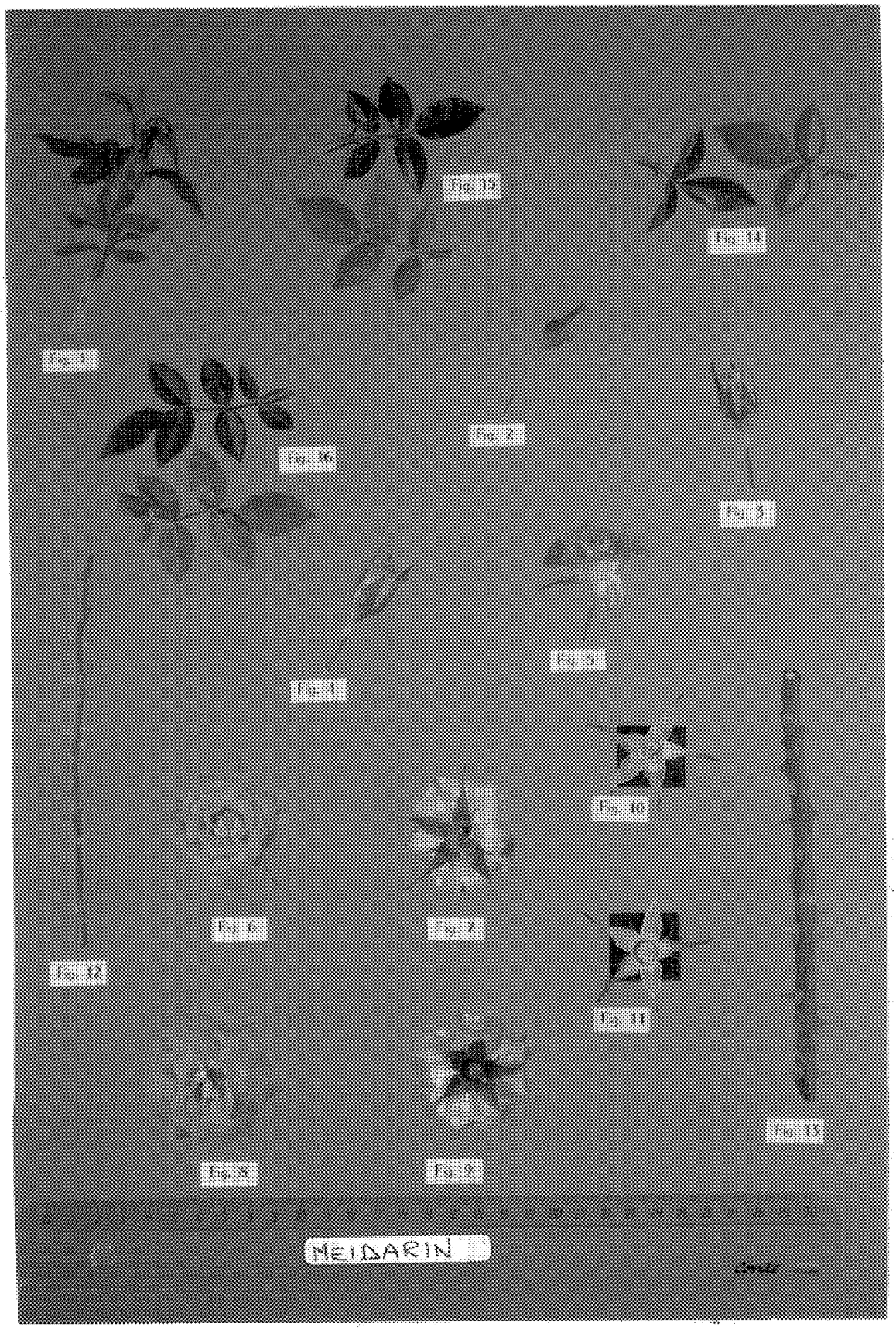
MEIDARIN